United States Patent [19]

Chu et al.

[11] Patent Number: 4,982,033

[45] Date of Patent: Jan. 1, 1991

[54] PROCESS FOR CONVERTING LIGHT ALIPHATICS TO AROMATICS

[75] Inventors: Cynthia T-W. Chu, Princeton Junction; Thomas F. Degnan, Moorestown, both of N.J.; Billy K. Huh, Birmingham, Ala.

[73] Assignee: Mobil Oil Corp., Fairfax, Va.

[21] Appl. No.: 469,651

[22] Filed: Jan. 24, 1990

Related U.S. Application Data

[63] Continuation-in-part of Ser. No. 254,524, Oct. 6, 1988, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ ............................................ C07C 15/393
[52] U.S. Cl. .................... 585/419; 585/407; 585/418; 585/661
[58] Field of Search ............... 585/407, 418, 419, 661

[56] References Cited

U.S. PATENT DOCUMENTS

| | | | |
|---|---|---|---|
| 3,756,942 | 9/1973 | Cattanach | 258/137 |
| 4,329,532 | 5/1982 | Conn et al. | 585/407 |
| 4,334,115 | 6/1982 | Cobb | 585/415 |
| 4,439,409 | 3/1984 | Puppe et al. | 423/328 |
| 4,530,756 | 7/1985 | Chang et al. | 585/475 |
| 4,788,370 | 11/1988 | Chang et al. | 585/415 |
| 4,826,667 | 5/1989 | Zones et al. | 423/326 |
| 4,897,177 | 1/1990 | Nadler | 585/407 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

Primary Examiner—Anthony McFarlane
Attorney, Agent, or Firm—Alexander J. McKillop; Charles J. Speciale; Dennis P. Santini

[57] ABSTRACT

Aliphatic $C_2$ to $C_{12}$ hydrocarbons are converted in the presence of a particular zeolite catalyst to a mixture of aromatics, optionally containing olefins.

18 Claims, 2 Drawing Sheets

PROCESS FOR CONVERTING LIGHT ALIPHATICS TO AROMATICS

CROSS-REFERENCE TO RELATED APPLICATIONS

This application is a continuation-in-part of U.S. patent application Ser. No. 254,524, filed Oct. 6, 1988, which is a continuation-in-part of U.S. patent application Ser. No. 98,176, filed Sept. 18, 1987, now abandoned, which is a continuation-in-part of U.S. patent application Ser. No. 890,268, filed July 29, 1986, now abandoned.

BACKGROUND OF THE INVENTION

This invention relates to a process for converting a paraffinic feed containing a major proportion of $C_2$ to $C_{12}$ aliphatic hydrocarbons, e.g., a Udex raffinate, to aromatics, or mixture of aromatics and olefins, in the presence of a zeolite catalyst.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded ZSM-5 is one such example wherein the $SiO_2/Al_2O_3$ ratio is at least 5 and up to the limits of present analytical measurement techniques. U.S. Pat. No. 3,941,871 (Reissue U.S. Pat. No. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

Zeolites and alumina have been used in the past in the preparation of catalysts for the production of aromatic hydrocarbons from aliphatic hydrocarbons. The aliphatic hydrocarbon is passed over the catalyst at an elevated temperature in the liquid or vapor phase. Zeolites of various types have been suggested for the preparation of such catalysts. Examples of such zeolites are mordenite and ZSM-5.

U.S. Pat. No. 3,756,942 discloses a process for converting paraffinic feedstocks over zeolites such as ZSM-5 to produce a variety of hydrocarbon products. The underlying chemistry involved in this conversion is extremely complex. More particularly, a number of simultaneous and sometimes competing reactions take place to produce a variety of products which can, in turn, be reacted to form still different products. These possible reactions include cracking of paraffins, aromatization of olefins, and alkylation and dealkylation of aromatics. Products from the conversion of $C_5{}^+$ paraffinic feedstocks over ZSM-5 include $C_6$–$C_8$ aromatics, $C_2$–$C_4$ olefins, $C_9{}^+$ aromatics and $C_1$–$C_3$ paraffins. Of these products the $C_6$–$C_8$ aromatics and $C_2$–$C_4$ olefins are the most desired.

$C_6$–$C_8$ aromatics, e.g., benzene, toluene, xylene and ethyloenzene, also referred to collectively as BTX, are valuable organic chemicals which can be used in a variety of ways. Since BTX has a high octane value it can be used as a blending stock for making high octane gasoline.

$C_2$–$C_4$ olefins, e.g., ethylene, propylene and butene, are also valuable organic chemicals which can be used to form polymers. By way of contrast, $C_1$–$C_3$ paraffins (i.e., methane, ethane and propane), particularly in admixture, are less valuable chemicals which are generally used for fuel.

According to U.S. Pat. No. 3,755,486, $C_{6-10}$ hydrocarbons undergo dehydrocyclization to benzene and alkylbenzenes in the presence of a Li, Na or K zeolite X or Y or faujasite impregnated with 0.3 to 1.4 percent Pt.

U.S. Pat. No. 3,760,024 discloses the aromatization of a feed containing $C_{2-4}$ paraffins and/or olefins in the absence of added hydrogen employing ZSM-5 as catalyst.

According to U.S. Pat. No. 3,855,115, aromatization of hydrocarbons is accomplished employing rhenium-exchanged ZSM-5.

Aliphatic naphthas are upgraded to products of increased aromatics content by the process disclosed in U.S. Pat. No. 3,890,218. The process employs a zeolite catalyst such as ZSM-5 into which one or more metals which increase the aromatization activity of the zeolite, e.g., zinc or cadium, have been incorporated.

In the process disclosed in U.S. Pat. No. 4,347,394 light straight-run naphthas and similar mixtures are converted to highly aromatic mixtures, principally benzene, employing a Group VIII metal-containing intermediate pore size zeolite, e.g. ZSM-5, which has been rendered substantially free of acidity by treatment with an alkali metal compound, e.g., NaOH.

Gaseous feedstocks containing ethane are converted to a mixture of benzene, toluene and xylene ("BTX") in the process of U.S. Pat. No. 4,350,835 utilizing a gallium-containing zeolite such as ZSM-5. A similar catalyst further containing thorium is disclosed in U.S. Pat. No. 4,629,818.

U.S. Pat. No. 4,435,283 describes a method for dehydrocyclizing alkanes employing as catalyst a Group VIII metal-containing large pore zeolite which further contains an alkaline earth metal, e.g., zeolite X, Y or L containing Pt and barium.

SUMMARY OF THE INVENTION

In accordance with the present invention, a process is provided for producing one or more aromatic compounds alone or in admixture with one or more olefins which comprises contacting under suitable conversion conditions a feedstock containing a substantial amount of at least one $C_2$–$C_{12}$ aliphatic hydrocarbon with a conversion catalyst to provide said aromatic compound(s) and/or mixture of aromatic compound(s) and olefin(s), said catalyst comprising a synthetic porous crystalline material characterized by an X-ray diffraction pattern including values substantially as set forth in Table I, infra.

DESCRIPTION OF SPECIFIC EMBODIMENTS

Figure 1:
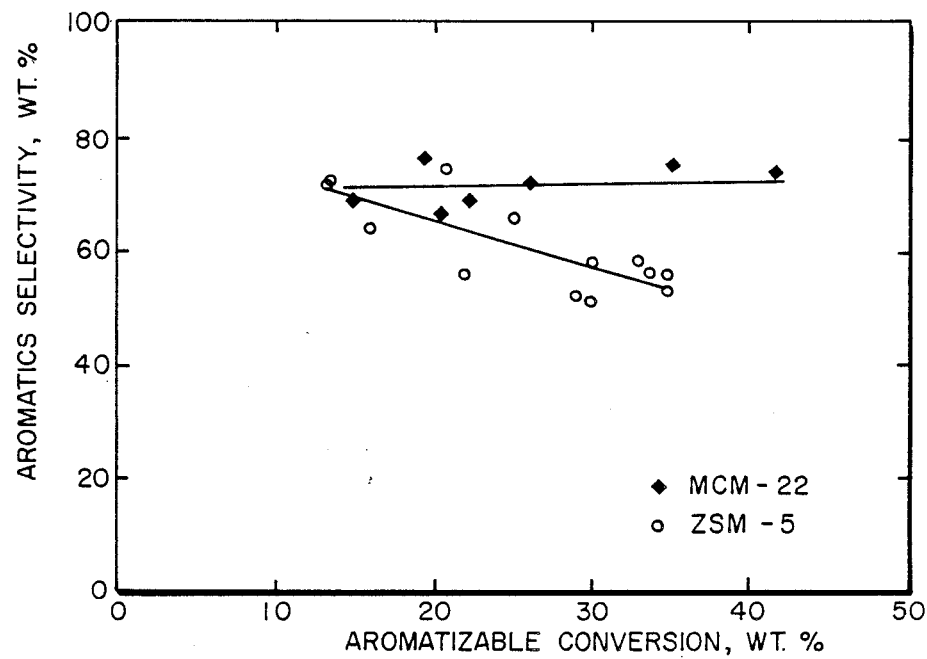
FIGS. 1–3 are graphical representations of process performance data relating to the aliphatic hydrocarbon conversion process of this invention.

The entire contents of applications Ser. Nos. 254,524; 98,176; and 890,268 are incorporated herein by reference.

The feed stream to the process of this invention contains at least 20% and more preferably at least 50% by weight of at least one aliphatic hydrocarbon containing 2 to 12 carbon atoms. The hydrocarbon may be straight chain, open chain or cyclic and may be saturated or unsaturated. Some contemplated hydrocarbons are ethane, propane, propylene, n-butane, n-butenes, isobutane, isobutene, straight chain, branched chain and cyclic pentanes, pentenes, hexanes, hexenes, heptanes, heptenes, octanes, octenes, nonanes, nonenes, decanes, undecanes, decenes, undecenes, dodecanes and dodecenes. A particularly useful hydrocarbon feedstock herein is a raffinate from a hydrocarbon mixture which has had aromatics removed therefrom by a solvent extraction treatment. Examples of such solvent extraction treatments are described on pages 706–709 of the *Kirk-Othmer Encyclopedia of Chemical Technology*, Third Edition, Vol. 9, John Wiley and Sons, 1980. One such hydrocarbon feedstock is a Udex raffinate, a typical composition of which is as follows:

| Component | Wt. Percent |
|---|---|
| $C_5$ | 6.20 |

-continued

| Component | Wt. Percent |
|---|---|
| $C_5^=$ | 0.19 |
| $C_6$ | 45.80 |
| $C_6^=$ | 8.49 |
| $C_7$ | 27.93 |
| $C_7^=$ | 3.56 |
| $C_8$'s | 1.87 |
| Benzene | 0.39 |
| Toluene | 3.85 |
| EB | 0.34 |
| Xylene | 0.39 |
| $C_9^+$ Aromatics | 1.18 |

The synthetic porous crystalline material employed as catalyst in the process of this invention is referred to herein as "zeolite MCM-22" or simply "MCM-22".

Zeolite MCM-b 22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-b 22 has a formula, on an anhydrous basis and in terms of xoles of oxides per n moles of $YO_2$, as follows:

$$(0.005-0.1)Na_2O:(1-4)R:X_2O_3:nYO_2$$

wherein R is an organic. The Na and R components are associated with the zeolite as a result of their presence during crystallization, and are easily removed by post-crystallization methods hereinafter more particularly described.

Zeolite MCM-22 is thermally stable and exhibits high surface area of greater than 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations. It can, therefore, be used as a catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the activity of the catalyst for the conversion process herein. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, $I/I_o \times 100$ |
|---|---|
| 30.0 ± 2.2 | W-M |
| 22.1 ± 1.3 | W |

TABLE I-continued

| Interplanar d-Spacing (A) | Relative Intensity, I/Io × 100 |
|---|---|
| 12.36 ± 0.2 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.2 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) The interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:

W=0-20

M=20-40

S=40-60

VS=60-100

It should be understood that these X-ray diffraction patterns are characteristic of all species of zeolite MCM-22. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Prior to its use as catalyst herein, the MCM-22 crystals should be subjected to thermal treatment to remove part or all of any organic constituent present therein.

The zeolite MCM-22 catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of cocrystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

Zeolite MCM-22, especially in its metal, hydrogen and ammonium forms, can be beneticially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the process of this invention, the zeolite MCM-22 crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of xole ratios of oxides, within the following ranges:

| Reactants | Useful | Preferred |
|---|---|---|
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt.% solid $YO_2$. Where $YO_2$ is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel, such as, e.g., polypropylene jars or teflon lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight of the crystalline product.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Iyler) screen. In cases where the catalyst is molded, such as by extrusion, the crystals can be extruded before drying or partially dried and then extruded.

It may be desired to incorporate the MCM-22 crystalline material with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter my be either naturally occurring or in the form of gelatinous precipitates or gels including mixtures of silica and metal oxides. Use of a material in conjunction with zeolite MCM-22, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with MCM-22 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite MCM-22 also include inorganic oxides, notably alumina.

In addition to the foregoing materials, the MCM-22 crystals can be composited with a porous matrix material such as silica-alumina, silica-magnesia, silica-zirconia, silica-thoria, silica-beryllia, silica-titania as well asternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the alkylation catalyst of the invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

The hydrocarbon conversion process of this invention is conducted so that a feed containing at least 20 wt.% and more preferably at least 50 wt.%, of one or more $C_2$–$C_{12}$ aliphatic hydrocarbons is contacted with zeolite MCM-22 in a reaction zone, such as, for example, a fixed or fluid bed of catalyst composition under effective conversion conditions. In a typical embodiment of the process of this invention, the feed stream is introduced into the reaction zone at a temperature within the range of from about 316° C. (600° F.) to about 760° C. (1400° F.), a pressure within the range of from about atmospheric to about 400 psig and a liquid hourly space velocity (LHSV) of from about 0.1 hr$^{-1}$ to about 5 hr$^{-1}$.

Preferred temperatures for the process of this invention fall within the range of about 400° C. (752° F.) to about 676.7° C. (1250° F.) and preferred pressures fall within the range of from about 20 to about 100 psig. A preferred LHSV is from about 0.3 to about 3.

In order to more fully illustrate the hydrocarbon conversion process of this invention and the manner of practicing same, the following examples are presented. In examples illustrative of the synthesis of zeolite MCM-22, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt.% for water vapor, greater than about 4.5 wt.%, usually greater than about 7 wt.% for cyclohexane vapor and greater than about 10 wt.% for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant =0.016 sec$^{-1}$.). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO_2/Al_2O_3 = 30.0$ $OH^-/SiO_2 = 0.18$ $H_2O/SiO_2 = 44.9$ $Na/SiO_2 = 0.18$ $R/SiO_2 = 0.35$ where R is hexaxethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table III. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the calcined crystalline material was measured to be 494 m$^2$/g.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = 21.1 | |

TABLE III

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |

TABLE III-continued

| Degrees 2-Theta | Interplanar d-Spacing (A) | I/I$_o$ |
|---|---|---|
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C., and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table IV. The sorption and surface area measurements were of the calcined product.

TABLE IV

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, m$^2$/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of H$_2$O. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table V:

TABLE V

| Product Composition uncalcined | |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption, wt. % | |
| Cyclohexane | 9.1 |
| N-Hexane | 14.9 |
| H$_2$O | 16.8 |
| Surface Area, m$^2$/g | 479 |

EXAMPLE 8

Twenty-five grams of solid crystal product from Example 7 were calcined in a flowing nitrogen atmospheres at 538° C. for 5 hours, followed by purging with 5% oxygen gas (balance N$_2$) for another 16 hours at 538° C.

Individual 3 g samples of the calcined material were ion-exchanged with 100 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
|---|---|---|---|
| Ionic Composition, wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite has very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts H$_2$O. To this was added 8.56 parts of Ultrasil silica, and the mixture was thoroughly homogenized. A 3.88 parts quantity of hexamethyleneimine was added to the mixture.

The reaction mixture had the following composition in mole ratios:

SiO$_2$/B$_2$O$_3$ = 6.1

OH$^-$/SiO$_2$ = 0.06

$H_2O/SiO_2 = 19.0$ $K/SiO_2 = 0.06$ $R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405m²/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = 1406 | |
| $SiO_2/(Al+B)_2O_3$, molar ratio = 25.8 | |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_2/B_2O_3 = 12.3$ $OH^-/SiO_2 = 0.056$ $H_2O/SiO_2 = 18.6$ $K/SiO_2 = 0.056$ $R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ (12 Torr) | 14.4 wt. % |
| Cyclohexane (40 Torr) | 4.6 wt. % |

| -continued | |
|---|---|
| n-Hexane (40 Torr) | 14.0 wt. % |

The surface area of the calcined crystalline material was measured to be 438m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = 249 | |
| $SiO_2/(Al+B)_2O_3$, molar ratio = 28.2 | |

EXAMPLE 14

A portion of the calcined crystalline product of Example 13 was tested in the Alpha Test and found to have an Alpha Value of 5.

EXAMPLES 15-19 AND COMPARISON EXAMPLES 20-26

Examples 15 to 19 illustrate the conversion of the Udex raffinate whose composition is set forth above over zeolite MCM-22 to provide a product mixture containing substantial amounts of BTX aromatics together with other aromatic and aliphatic hydrocarbons. Examples 20 to 26 illustrate the use of unbound ZSM-5 for conversion of the same feedstock under the same conditions.

The zeolite MCM-22 used in Examples 15-19 was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexaxethyleneimine was removed from the autoclave by controlled distillation and the zeolite crystals separated from the remaining liquid by filtration, washed with deionized $H_2O$ and dried. The zeolite was then calcined in nitrogen at 540° C., exchanged with an aqueous solution of ammonium nitrate and calcined in air at 540° C. The zeolite was tabletted, crushed and sized to 30/40 mesh and loaded into the fixed-bed downflow reactor at a constant MCM-22 loading of 0.5 gm.

The MCM-22 catalyst had the following properties (Table VI):

TABLE VI

| Properties of the MCM-22 Conversion Catalyst | |
|---|---|
| Surface Area (BET), m²/g | 503 |
| $SiO_2/Al_2O_3$ (molar) | 27 |
| Na, ppm | 495 |
| Alpha | 693 |
| Sorption Properties, wt. % | |
| $H_2O$ | 15.0 |
| $CyC_6$ | 12.5 |
| $n-C_6$ | 16.0 |
| Ash at 1000° C., wt. % | 99.05 |

Zeolite ZSM-5 which was used in Examples 20 to 26 ($SiO_2Al_2O_3 = 55$) was prepared in a conventional manner.

Reaction conditions for Examples 15 to 26 were 538° C., 1 atm and 2-30 WHSV.

The analyses of the conversion products of Examples 15-26 is set forth in Table VII as follows:

also at 482° C. (900° F.). The calcination was completed by raising the temperature to 540° C. (1000° F.) at 5°F./min and finally switching to 100% air (3 v/v/min) and holding at 540° C. (1000° F.) for three hours.

TABLE VII

Conversion of Udex Raffinate Over Zeolite Catalysts

| Example | 15 | 16 | 17 | 18 | 19 | 20 | 21 | 22 | 23 | 24 | 25 | 26 |
|---|---|---|---|---|---|---|---|---|---|---|---|---|
| Zeolite | MCM-22 | MCM-22 | MCM-22 | MCM-22 | MCM-22 | ZSM-5 | ZSM-5 | ZSM-5 | ZSM-5 | ZSM-5 | ZSM-5 | ZSM-5 |
| WHSV | 26 | 13 | 6.6 | 2.6 | 1.3 | 26 | 26 | 13 | 13 | 6.6 | 6.6 | 2.6 |
| Pressure | atm | atm | atm | atm | atm | atm | atm | atm | atm | atm | atm | atm |
| Temperature, °C. | 538 | 538 | 538 | 538 | 538 | 538 | 538 | 538 | 538 | 538 | 538 | 538 |
| TOS, hr | 1 | 3 | 4 | 7 | 9 | 1 | 2 | 4 | 5 | 6 | 8 | 10 |
| Product Analysis, wt. % | | | | | | | | | | | | |
| Hydrogen | 0.49 | 0.62 | 0.87 | 1.33 | 1.58 | 0.55 | 0.59 | 0.38 | 0.83 | 0.11 | 0.52 | 0.11 |
| Methane | 1.40 | 2.18 | 2.27 | 2.82 | 3.48 | 1.03 | 0.95 | 1.80 | 1.45 | 3.07 | 2.76 | 5.09 |
| Ethane | 2.58 | 3.82 | 4.00 | 4.59 | 5.60 | 2.20 | 2.17 | 3.58 | 3.06 | 5.87 | 5.22 | 8.41 |
| Ethylene | 3.11 | 3.59 | 3.36 | 2.71 | 2.28 | 3.23 | 3.21 | 4.26 | 3.57 | 4.93 | 4.56 | 4.77 |
| Propane | 9.97 | 14.24 | 15.05 | 15.60 | 16.36 | 7.51 | 7.19 | 12.02 | 10.22 | 18.34 | 16.96 | 25.10 |
| Propylene | 7.95 | 7.54 | 6.43 | 4.48 | 3.39 | 7.76 | 7.77 | 9.33 | 7.77 | 9.59 | 8.92 | 7.55 |
| Butanes | 8.72 | 9.57 | 7.75 | 6.60 | 5.99 | 6.27 | 6.17 | 9.44 | 7.94 | 12.42 | 11.63 | 13.17 |
| Butenes | 4.60 | 4.53 | 3.80 | 2.44 | 2.09 | 4.90 | 4.92 | 5.50 | 4.89 | 4.99 | 5.24 | 4.15 |
| Pentanes | 4.97 | 4.15 | 3.46 | 2.40 | 2.01 | 4.92 | 4.87 | 4.98 | 4.60 | 4.37 | 4.49 | 3.30 |
| Pentenes | 1.48 | 1.42 | 1.15 | 0.80 | 0.61 | 1.81 | 1.84 | 1.79 | 1.73 | 1.54 | 1.60 | 1.12 |
| Hexanes | 27.43 | 20.30 | 20.44 | 16.16 | 14.37 | 33.74 | 33.63 | 25.27 | 26.17 | 16.08 | 16.12 | 7.95 |
| Hexenes | 2.85 | 2.24 | 1.98 | 2.20 | 1.67 | 0.60 | 0.76 | 0.40 | 0.52 | 0 | 0 | 0.18 |
| Heptanes | 13.27 | 10.22 | 10.05 | 10.79 | 9.02 | 14.72 | 14.90 | 10.32 | 11.26 | 6.57 | 5.73 | 3.20 |
| Heptenes | 0.73 | 0.67 | 0.69 | 1.35 | 1.01 | 0.89 | 0.92 | 0.76 | 0.81 | 0 | 0 | 0.37 |
| Benzene | 1.26 | 2.08 | 2.60 | 4.42 | 5.88 | 1.01 | 1.01 | 1.56 | 1.56 | 2.16 | 2.05 | 3.44 |
| Toluene | 4.43 | 5.90 | 7.07 | 10.28 | 13.28 | 4.61 | 4.61 | 6.25 | 6.46 | 6.13 | 6.95 | 7.78 |
| Ethylbenzene | 0.39 | 0.63 | 0.91 | 1.10 | 1.18 | 0.32 | 0.32 | 0.49 | 0.52 | 0.30 | 0.49 | 0.39 |
| Xylenes | 2.18 | 3.44 | 4.33 | 4.97 | 5.89 | 1.78 | 1.85 | 0.32 | 3.59 | 2.02 | 3.75 | 3.08 |
| Trimethylbenzenes | 1.16 | 1.63 | 3.79 | 2.47 | 2.08 | 1.12 | 1.11 | 1.16 | 2.00 | 0.90 | 1.84 | 0.74 |
| $C_{10}^+$ Aromatics | 1.03 | 1.24 | 0 | 2.66 | 2.22 | 1.03 | 1.20 | 0.39 | 1.05 | 0.62 | 1.18 | 0.34 |

Figure 2:
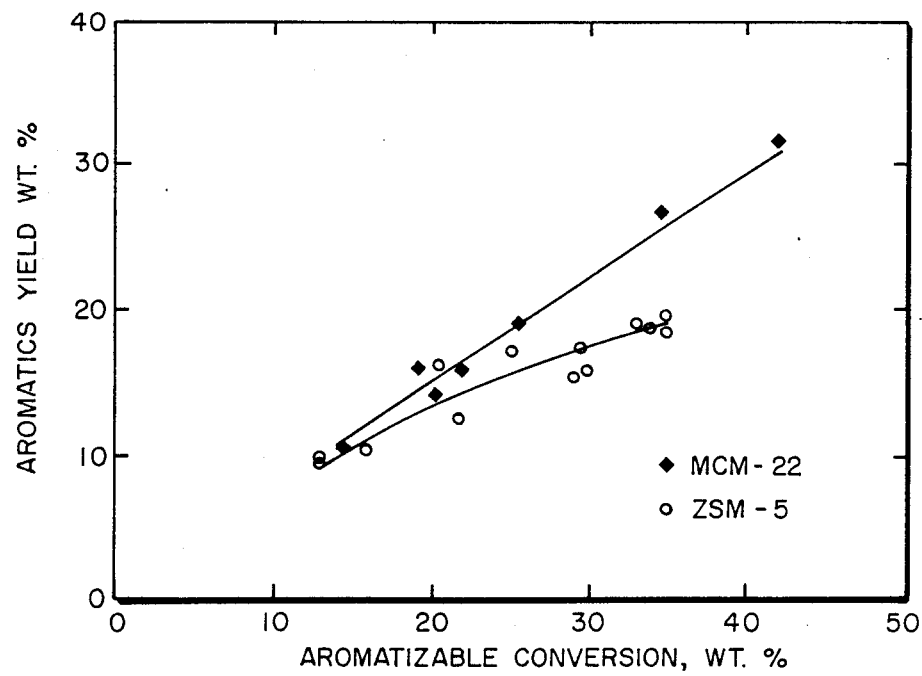

FIG. 1 compares aromatics selectivity for both ZSM-5 and MCM-22. At 25 to 40% aromatizable conversion, MCM-22 shows significantly higher aromatics selectivity than the ZSM-5. Similarly, FIG. 2 shows that aromatics yield is also enhanced substantially employing MCM-22.

In the Figures, Aromatic Selectivity and Aromatizables are defined as follows:

$$\text{Aromatic Selectivity} = \frac{\text{Aromatics Yield}}{(C_1 + C_2 + \text{Aromatics Yield})}$$

all terms in weight percent of product, and

Aromatizables = ethylene + higher molecular weight non-aromatic compounds (e.g. $C_3$+non-aromatics).

EXAMPLES 27-29

These examples illustrate the conversion of n-hexane over a catalyst containing the zeolite of the invention. The zeolite was produced by adding 4.49 parts, by weight, of hexamethyleneimine to a mixture containing 1.00 part sodium aluminate, 1.00 part 50% NaOH, 8.54 parts Ultrasil VN3 silica and 44.19 parts deionized $H_2O$. The reaction mixture was heat to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried.

Figure 3:
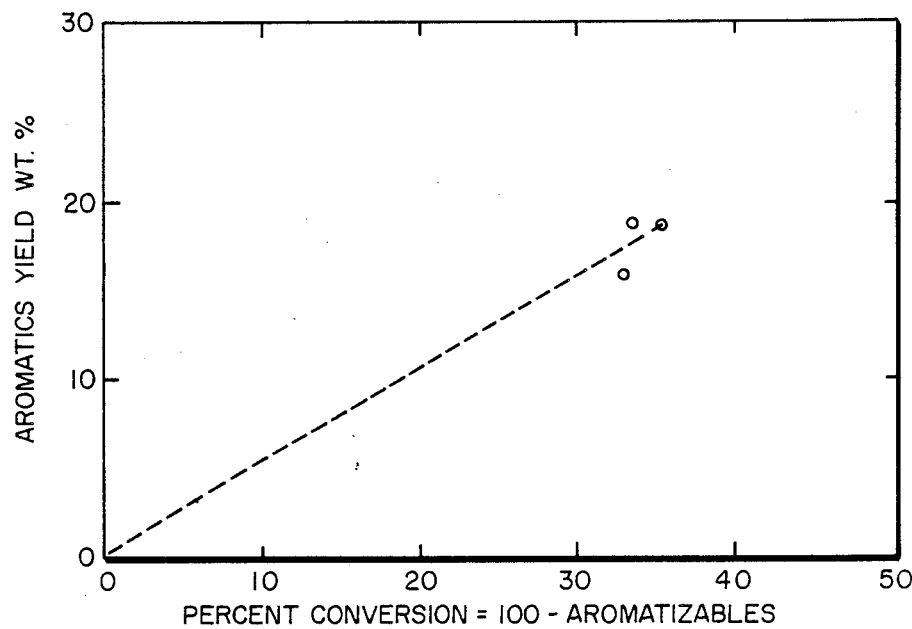

A portion of the zeolite crystals was combined with $Al_2O_3$ to form a mixture of 65 parts, by weight, zeolite and 35 parts $Al_2O_3$. Water was added to this mixture to allow the resulting catalyst to be formed into extrudates. The catalyst was activated by calcining at 482° C. (900° F.) in 3 v/v/min nitrogen for three hours, then treated with 50% vol.% air/50 vol.% $N_2$ at 3 v/v/min, In each of the examples, the n-hexane conversion was effected at 540° C., 100 kPa (atmospheric) pressure and an LHSV of 0.6. Table VIII sets forth the results of the conversions and FIG. 3 shows the yield of aromatics against the percentage of conversion for the combined results.

TABLE VIII

| | Example | | |
|---|---|---|---|
| | 27 | 28 | 29 |
| | Time on Stream (hrs) | | |
| Products: | 6 | 30 | 54 |
| $H_2$ | 0.67 | 0.58 | 0.55 |
| Methane | 3.97 | 3.24 | 3.71 |
| Ethane | 12.34 | 11.38 | 12.68 |
| Propane | 24.84 | 23.97 | 27.08 |
| Butanes | 11.05 | 9.27 | 8.90 |
| Pentanes | 1.52 | 1.04 | 0.93 |
| n-Hexane | 7.24 | 5.44 | 6.81 |
| $C_6$+ P+O | 1.29 | 2.51 | 2.75 |
| Ethylene | 4.42 | 4.63 | 4.72 |
| Propylene | 7.48 | 8.90 | 7.16 |
| $C_4$ Olefins | 4.51 | 7.07 | 5.61 |
| $C_5$ Olefins | 1.32 | 2.44 | 2.35 |
| Benzene | 2.30 | 2.55 | 2.52 |
| Toluene | 5.31 | 4.88 | 4.25 |
| $A_8$ | 4.65 | 5.15 | 4.86 |
| $A_9+$ | 7.09 | 6.95 | 5.12 |
| Aromatics selectivity | 54.25 | 57.19 | 50.54 |

EXAMPLE 30

This example illustrates the use of the present zeolite for n-hexane conversion after the zeolite has been steamed (100% steam) at 540° C. (1000° F.) for 48 hours. The reaction conditions were essentially the same as those employed in Examples 27-29.

The results of the conversion herein are set forth in Table IX as follows:

TABLE IX

| Products: | Time On Stream (hrs.) 6 |
|---|---|
| $H_2$ | 0.11 |
| Methane | 2.02 |
| Ethane | 4.96 |
| Propane | 8.13 |
| Butanes | 2.33 |
| Pentanes | 0.16 |
| n-Hexane | 52.30 |
| $C_6+$ P+O | 2.36 |
| Ethylene | 4.02 |
| Propylene | 11.18 |
| $C_4$Olefins | 1.96 |
| $C_5$Olefins | 0.22 |
| Benzene | 2.44 |
| Toluene | 5.09 |
| $A_8$ | 1.94 |
| $A_9+$ | 0.78 |
| Aromatics selectivity | 59.49 |

WHAT IS CLAIMED IS:

1. A process for producing one or more aromatic compounds alone or in admixture with one or more olefins which comprises contacting under suitable conversion conditions a feedstock containing a substantial amount of at least one $C_2$–$C_{12}$ aliphatic hydrocarbon with a conversion catalyst to provide said aromatic compound(s) and/or mixture of aromatic compound(s) and olefin(s), said catalyst comprising a synthetic porous crystalline material characterized by an X-ray diffraction pattern including values substantially as set forth in Table I of the specification.

2. The process of claim 1 wherein the synthetic porous crystalline material is characterized by an X-ray diffraction pattern including values substantially as set forth in Table II of the specification.

3. The process of claim 1 wherein the synthetic porous crystalline material has a composition comprising the molar relationship $$X_2O_3:(n)YO_2,$$

wherein n is at least about 10, X is a trivalent element and Y is a tetravalent element.

4. The process of claim 2 wherein the synthetic porous crystalline material has a composition comprising the molar relationship:

$$X_2O_3:(n)YO_2,$$

wherein n is at least about 10, X is a trivalent element and Y is a tetravalent element.

5. The process of claim 1 wherein the synthetic porous crystalline material possesses equilibrium adsorption capacities of greater than about 4.5 wt.% for cyclohexane vapor and greater than about 10 wt.% for n-hexane vapor.

6. The process of claim 3 wherein X is selected from the group consisting of aluminum, boron, gallium and combinations thereof and Y is selected from the group consisting of silicon, germanium and combinations thereof.

7. The process of claim 3 wherein X comprises aluminum and Y comprises silicon.

8. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

9. The process of claim 1 wherein said synthetic porous crystalline material has been thermally treated at a temperature up to about 925° C. in the presence or absence of steam.

10. The process of claim 8 wherein said synthetic porous crystalline material has been-thermally treated at a temperature up to about 925° C. in the presence or absence of steam.

11. The process of claim 1 wherein said synthetic porous crystalline material is combined with a matrix material.

12. The process of claim 11 wherein said matrix material is a silica or alumina-containing material.

13. The process of claim 12 wherein the catalyst is provided in the form of extrudate, beads or fluidizable microspheres.

14. The process of claim 1 wherein the feedstock contains at least about 50% by weight of at least one $C_2$–$C_{12}$ aliphatic hydrocarbon.

15. The process of claim 1 wherein the feedstock is a raffinate from a hydrocarbon mixture from which one or more aromatics have been removed by solvent extraction.

16. The process of claim 1 wherein the feedstock is a Udex raffinate.

17. The process of claim 1 carried out at a temperature of from about 600° F. to about 1400° F., a pressure of from atmospheric to about 400 psig and an LHSV of from about 0.1 hr$^-$to about 5 hr$^{-1}$.

18. The process of claim 11 wherein said matrix material comprises zirconia, titania or mixtures thereof.

* * * * *